(12) United States Patent
Chae et al.

(10) Patent No.: US 9,326,941 B2
(45) Date of Patent: May 3, 2016

(54) HIGH-EFFICIENCY NANOPARTICLE-TYPE DOUBLE-HELICAL OLIGO-RNA STRUCTURE AND METHOD FOR PREPARING SAME

(71) Applicant: BIONEER CORPORATION, Daejeon (KR)

(72) Inventors: Jeiwook Chae, Daejeon (KR); Boram Han, Bucheon-si (KR); Han-na Kim, Jeonju-si (KR); Han Oh Park, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

(21) Appl. No.: 14/370,035

(22) PCT Filed: Jan. 4, 2013

(86) PCT No.: PCT/KR2013/000035
§ 371 (c)(1),
(2) Date: Jun. 30, 2014

(87) PCT Pub. No.: WO2013/103249
PCT Pub. Date: Jul. 11, 2013

(65) Prior Publication Data
US 2015/0005364 A1 Jan. 1, 2015

(30) Foreign Application Priority Data
Jan. 5, 2012 (KR) ........................ 10-2012-0001711

(51) Int. Cl.
| | |
|---|---|
| A61K 48/00 | (2006.01) |
| C07H 21/02 | (2006.01) |
| C07H 21/04 | (2006.01) |
| A61K 9/14 | (2006.01) |
| C12N 15/11 | (2006.01) |
| C12N 15/113 | (2010.01) |

(52) U.S. Cl.
CPC .............. *A61K 9/14* (2013.01); *C12N 15/111* (2013.01); *C12N 15/113* (2013.01); *C12N 2310/11* (2013.01); *C12N 2310/14* (2013.01); *C12N 2310/3515* (2013.01); *C12N 2320/30* (2013.01); *C12N 2320/32* (2013.01); *C12N 2330/30* (2013.01)

(58) Field of Classification Search
CPC . C12N 2310/11; C12N 15/111; C12N 15/113
See application file for complete search history.

(56) References Cited

U.S. PATENT DOCUMENTS

| | | |
|---|---|---|
| 5,660,985 A | 8/1997 | Pieken et al. |
| 5,808,023 A | 9/1998 | Sanghvi et al. |
| 5,958,691 A | 9/1999 | Pieken et al. |
| 6,175,001 B1 | 1/2001 | Barbas et al. |
| 6,221,959 B1 | 4/2001 | Kabanov et al. |
| 6,326,358 B1 | 12/2001 | Manoharan |
| 6,531,584 B1 | 3/2003 | Cook et al. |
| 2007/0041932 A1 | 2/2007 | Jeong et al. |
| 2007/0287681 A1 | 12/2007 | Jeong et al. |
| 2011/0268772 A1 | 11/2011 | Kim et al. |
| 2012/0108803 A1 | 5/2012 | Han et al. |
| 2012/0225129 A1 | 9/2012 | Eliasof et al. |

FOREIGN PATENT DOCUMENTS

| | | |
|---|---|---|
| CA | 2761749 A1 | 11/2010 |
| KR | 10-2007-0061770 A | 6/2007 |
| KR | 10-2009-0042297 A | 4/2009 |
| KR | 10-2010-0076905 A | 7/2010 |
| KR | 10-2010-0123214 A | 11/2010 |
| WO | 2007021142 A1 | 2/2007 |

OTHER PUBLICATIONS

Amarzguioui, M., et al, "Tolerance for mutations and chemical modifications in a siRNA", "Nucleic Acids Research", Jan 15, 2003, pp. 589-595, vol. 31, No. 2.
Barik, S., "Silence of the transcripts: RNA interference in medicine", "J Mol Med (Berl).", Oct. 2005, pp. 764-773, vol. 83, No. 10.
Behlke, M., "Progress Towards in Vivo Use of siRNAs", "Molecular Therapy", Feb. 14, 2006, pp. 644-670, vol. 13, No. 4.
Bertrand, J., et al., "Comparison of antisense oligonucleotides and siRNAs in cell culture and in vivo", "Biochemical and Biophysical Research Communications", Aug. 30, 2002, pp. 1000-1004, vol. 296.
Braasch, D., et al., "Biodistribution of phosphodiester and phosphorothioate siRNA", "Bioorganic and Medicinal Chemistry Letters", Mar. 8, 2004, pp. 1139-1143, vol. 14.
Bramsen, J., et al., "A screen of chemical modifications identifies position-specific modification by UNA to most potently reduce siRNA off-target effects", "Nucleic Acids Research", May 7, 2010, pp. 5761-5773, vol. 38, No. 17.
Chen, P., et al., "Strand-specific 5'-O-methylation of siRNA duplexes controls guide strand selection and targeting specificity", "RNA", Dec. 19, 2007, pp. 263-274, vol. 14, No. 2.
Chiu, Y., et al., "siRNA function in RNAi: A chemical modification analysis", "RNA", Sep. 2003, pp. 1034-1048, vol. 9.
Crooke, S., "Progress in Antisense Technology", "Annu. Rev. Med.", Oct. 6, 2003, pp. 61-95, vol. 55.

(Continued)

*Primary Examiner* — Amy Bowman
(74) *Attorney, Agent, or Firm* — Hultquist, PLLC; Steven J. Hultquist

(57) ABSTRACT

Provided are a double-stranded oligo RNA structure and a method of preparing the same, and more specifically, a double-stranded oligo RNA structure in which a polymer compound is covalently bound to a double-stranded oligo RNA in order to improve stability in vivo and a cell delivery efficiency of the double-stranded oligo RNA, and a method of preparing the same.

The double-stranded oligo RNA structure having the optimized structure according to the present invention may not inhibit functions of the double-stranded oligo RNA, but effectively improve stability and cell membrane permeability of the double-stranded oligo RNA, such that the double-stranded oligo RNA may be delivered into the cell even at a low concentration dosage thereof to be significantly used as a tool for treatment of cancer, infectious diseases, and the like, as well as a new delivery system of the double-stranded oligo RNA.

33 Claims, 5 Drawing Sheets

(56) References Cited

OTHER PUBLICATIONS

Elbashir, S., et al., "Duplexes of 21-nucleotide RNAs mediate RNA interference in cultured mammalian cells", "Nature", May 24, 2001, pp. 494-498, vol. 411.

Jeong, J., et al., "siRNA Conjugate Delivery Systems", "Bioconjugate Chem.", Jan. 2009, pp. 5-14, vol. 20, No. 1.

Kim, S., et al., "Local and systemic delivery of VEGF siRNA using polyelectrolyte complex micelles for effective treatment of cancer", "Journal of Controlled Release", Mar. 14, 2008, pp. 107-116, vol. 129, No. 2.

Opalinska, J., et al., "Nucleic-acid therapeutics: Basic principles and recent applications", "Nature Reviews Drug Discovery", Jul. 2002, pp. 503-514, vol. 1.

Soutschek, J., et al., "Therapeutic silencing of an endogenous gene by systemic administration of modified siRNAs", "Nature", Nov. 11, 2004, pp. 173-178, vol. 432, No. 7014.

Vaish, N., et al., "Improved specificity of gene silencing by siRNAs containing unlocked nucleobase analogs", "Nucleic Acids Research", Nov. 2, 2010, pp. 1823-1832, vol. 39, No. 5.

Watts, J., et al., "Chemically modified siRNA: tools and applications", "Drug Discovery Today", Jul. 7, 2008, pp. 842-855, vol. 13, No. 19/20.

Xie, F., et al., "Harnessing in vivo siRNA delivery for drug discovery and therapeutic development", "Drug Discovery Today", Jan. 2006, pp. 67-73, vol. 11, No. 1/2.

Zelphati, O., et al., "Mechanism of oligonucleotide release from cationic liposomes", "Proc. Natl. Acad. Sci. USA", Oct. 15, 2006, pp. 11493-11498, vol. 93, No. 21.

Loennberg, H., "Solid-phase synthesis of oligonucleotide conjugates useful for delivery and targeting of potential nucleic acid therapeutics", Bioconjugate Chemistry, Jun. 2009, pp. 1065-1094, vol. 20, No. 6.

Raouane, M., et al., "Synthesis, characterization, and in vivo delivery of siRNA-squalene nanoparticles targeting fusion oncogene in papillary thyroid carcinoma", J. Med. Chem., May 18, 2011, pp. 4067-4076, vol. 54.

Kawamata, T., et al., "Making RISC", Trends in Biochemical Sciences, Apr. 13, 2010, pp. 368-376, vol. 35, No. 7.

Rivas, F., et al., "Purified Argonaute2 and an siRNA form recombinant human RISC", Nat. Struct. Mol. Biol., Mar. 30, 2005, pp. 340-349, vol. 12, No. 4.

HIGH-EFFICIENCY NANOPARTICLE-TYPE DOUBLE-HELICAL OLIGO-RNA STRUCTURE AND METHOD FOR PREPARING SAME

CROSS-REFERENCE TO RELATED APPLICATIONS

This application is a U.S. national phase under the provisions of 35 U.S.C. §371 of International Patent Application No. PCT/KR13/00035 filed Jan. 4, 2013, which in turn claims priority of Korean Patent Application No. 10-2012-0001711 filed Jan. 5, 2012. The disclosures of such international patent application and Korean priority patent application are hereby incorporated herein by reference in their respective entireties, for all purposes.

TECHNICAL FIELD

The present invention relates to a double-stranded oligo RNA structure with high efficacy which is chemically synthesized and is usefully utilized for treatment of cancer, an infectious disease, and the like.

In order to be effectively delivered into a cell, the double-stranded oligo RNA structure may have a structure in which hydrophilic materials and hydrophobic materials are conjugated to both ends of a double-stranded RNA by a simple covalent bond or a linker-mediated covalent bond and may be converted into a nanoparticle form in an aqueous solution by a hydrophobic interaction of the double-stranded oligo RNA structures.

In addition, the present invention relates to a pharmaceutical composition containing the double-stranded oligo RNA structure, a method of preparing the double-stranded oligo RNA structure, and a technology of delivering a double-stranded oligo RNA using the double-stranded oligo RNA structure.

BACKGROUND ART

Since a role of an RNA interference (hereinafter, referred to as 'RNAi') had been recognized, it was found that the RNA interference sequence-specifically acts on mRNA in various kinds of mammalian cells (Silence of the transcripts: RNA interference in medicine. J. Mol. Med., 2005, 83: 764-773).

When a long-chain double-stranded RNA is delivered into a cell, the delivered double-stranded RNA is converted into a small interfering RNA (hereinafter, referred to as 'siRNA') which is processed to 21 to 23 base pairs (bp) by Dicer endonuclease. siRNA has a short-chain double-stranded RNA having 19 to 27 bases and is coupled to an RNA-induced silencing complex (RISC), whereby a guide (antisense) strand recognizes and degrades a target mRNA to sequence-specifically inhibit expression of a target gene (Nucleic-acid therapeutics: basic principles and recent applications. Nature Reviews Drug Discovery. 2002. 1, 503-514).

The long-chain double-stranded RNA delivered from the outside has a problem of eliciting a non-sequence-specific immune stimulation through interferon expression in a mammal cell; however, it was found that the problem may be overcome by a short-stranded siRNA (Duplexes of 21-nucleotide RNAs mediate RNA interference in cultured mammalian cells. Nature. 2001. 411, 494-498).

It is known that a chemically synthesized siRNA has a double strand of about 19 to 27 base pairs and consists of a 2-nt(nucleotide) overhang structure at 3' end, and in order that the double-stranded siRNA expresses an activity, the structure may consist of 3'-hydroxyl groups (OH) and 5'-phosphate groups ($PO_4$) (Effect of asymmetric terminal structures of short RNA duplexes on the RNA interference activity and strand selection. Nucleic Acids Res 1 Oct. 2008: 5812-5821; Strand-specific 5'-O-methylation of siRNA duplexes controls guide strand selection and targeting specificity. RNA 1 Feb. 2008: 263-274).

It is known that a commercialized and synthesized siRNA has a structure in which hydroxyl groups are present at both ends, and when the synthesized siRNA is delivered into a cell, siRNA 5' end is phosphorylated by a phosphorylation enzyme (kinase) to express functions of siRNA (siRNA function in RNAi: A chemical modification analysis. RNA 2003. 9: 1034-1048).

Bertrand et al. found that as compared to an antisense oligonucleotide (ASO) on the same target gene, siRNA has an effect of significantly inhibiting mRNA expression in vitro and in vivo, and the corresponding effect is maintained for a long time (Comparison of antisense oligonucleotides and siRNAs in cell culture and in vivo. Biochem. Biophys. Res. Commun. 2002. 296: 1000-1004).

In addition, since siRNA is complementarily coupled to a target mRNA to sequence-specifically regulate an expression of the target gene, a mechanism of the siRNA has an advantage that a target to be capable of being applied may be remarkably increased as compared to the existing antibody-based medical product or chemical material (small molecular drug) (Progress Towards in Vivo Use of siRNAs. MOLECULAR THERAPY. 2006 13(4):664-670).

In order to develop the siRNA as a therapeutic agent despite of excellent effect and variously usable range of the siRNA, the siRNA is required to be effectively delivered into a target cell by improving stability of the siRNA and a cell delivery efficiency (Harnessing in vivo siRNA delivery for drug discovery and therapeutic development. Drug Discov Today. 2006 January; 11(1-2):67-73).

In addition, the siRNA still has a non-specific innate immune stimulation, such that 2-methoxy-, 2-fluoro-substituents have been developed to overcome the non-specific innate immune stimulation.

Since the siRNA is not capable of passing through a hydrophobic phospholipid bilayer of a cell due to negative charges thereof, it is difficult to be delivered into the cell through a simple diffusion.

In order to increase siRNA delivery efficiency in vivo or in vitro, various kinds of cell delivery materials have been developed. Liposomes, cationic surfactants, and the like, are commonly used, and the use of carrier, that is, a fusion method of a gene with liposome or a method of using lipid or a polymer having cations has been known, or a method. of chemically modifying siRNA. or a. method of using conjugate has been known (Mechanisms and strategies for effective delivery of antisense and siRNA oligonucleotides. Nucleic Acids Res. 2008 July; 36(12):4158-71).

Since the siRNA is not capable of passing through a hydrophobic phospholipid bilayer of a cell due to negative charges thereof, it is difficult to be delivered into the cell through a simple diffusion, such that in order to overcome the difficulty, methylphosphonate or peptide nucleic acid (PNA) is used in a basic binding structure of the siRNA. In addition, a carrier is used, for example, a fusion method of a gene with liposome or a method of using lipid. or a polymer having cations is used (Chemically modified siRNA: tools and applications. Drug Discov. Today. 2008 October; 13(19-20):842-855).

Among them, as a method of using a nanocarrier, a method of using various polymers such as liposome, cationic polymer complex, and the like, is to carry siRNA on a nanocarrier by formation of nanoparticles to deliver siRNA. Among the methods of using nanocarriers, a method of using polymeric nanoparticle, polymer micelle, lipoplex, or the like, is mainly used, wherein the lipoplex consists of cationic lipid to interact with anionic lipid of endosome of a cell, thereby eliciting a destabilization effect of the endosome to deliver the siRNA into a cell (Mechanism of oligonucleotide release from cationic liposomes. Proc. Natl. Acad. Sci. USA. 1996 Oct. 15; 93(21):11493-8).

In addition, it is known that chemical materials, and the like, are connected to end portions of a siRNA passenger (sense strand) to provide increased pharmacokinetics characteristics and high efficacy may be induced in vivo (Therapeutic silencing of an endogenous gene by systemic administration of modified siRNAs. Nature. 2004 Nov. 11; 432(7014): 173-8). Here, stability of the siRNA may vary depending on properties of the chemical materials bound to ends of the siRNA sense (passenger) or antisense (guide) strand. For example, a siRNA having a polymer compound such as polyethylene glycol (PEG) conjugated thereto interacts with an anionic phosphate group of siRNA in the presence of cationic materials to form a complex, thereby being a siRNA carrier having an improved stability (Local and systemic delivery of VEGF siRNA using polyelectrolyte complex micelles for effective treatment of cancer. J Control Release. 2008 Jul. 14; 129(2):107-16). In particular, micelle consisting of polymer complexes has an extremely small size, significantly uniform distribution, and is spontaneously form, thereby being easy to manage quality of formulation and secure reproducibility, as compared to other systems used as a drug delivery vehicle, such as microsphere, nanoparticle, and the like.

Recently, in order to improve an intracellular delivery efficiency of siRNA, technology of using a siRNA conjugate in which hydrophilic material which is a biocompatible polymer (for example, polyethylene glycol (PEG)) is conjugated to the siRNA by a simple covalent bond or a linker-mediated covalent bond, to thereby secure stability of siRNA and have effective cell membrane permeability was developed (see Korean Patent Publication No. 883471).

However, the chemical modification of siRNA and the conjugation with the polyethylene glycol (PEG) (PEGylation) still has disadvantages that stability in vivo is low and delivery into a target organ is not smooth. In chemical modification of siRNA, a bond to RISC without modification at 5' end of an antisense (guide) strand recognizing a target mRNA is significantly important to initiation of RNAi mechanism. In a case of a sense (passenger) strand, through the existing research, functions of siRNA are confirmed even in a case where the conjugates are bound to both of ends, such that the sense (passenger) strand is utilized for a conjugate bond (siRNA Conjugate Delivery Systems. Bioconjugate Chem., 2009, 20 (1), pp 5-14).

In a case of a double-stranded oligo RNA structure in which the hydrophilic materials and the hydrophobic materials are bound to the double-stranded oligo RNA, self-assembling nanoparticles are formed by a hydrophobic interaction of the hydrophobic materials, wherein the self-assembling nanoparticle is referred to as 'SAMiRNA' (Korean Patent Laid-Open Publication No. 2009-0042297).

The technology of forming the self-assembling nanoparticles (SAMiRNA) by binding the hydrophobic materials and the hydrophilic materials to an end of the double-stranded oligo RNA has a possibility of RNA strand bias of a double-stranded oligo RNA, that is, RNAi functions may be inhibited depending on a position where the hydrophilic materials and the hydrophobic materials are bound to the end. Therefore, a technology of delivering a double-stranded oligo RNA capable of effectively permeating a cell membrane without inhibiting the functions of the double-stranded oligo RNA through optimization of the double-stranded oligo RNA structure is inevitably required to be developed.

SUMMARY OF INVENTION

An object of the present invention is to provide a structure a self-assembling nanoparticle (SAMiRNA) with a maximized efficacy in vivo. The SAMiRNA of the present invention means a nanoparticle formed by a hydrophobic interaction among hydrophobic materials in double-stranded oligo RNA structures in which hydrophilic materials and hydrophobic materials are bound to ends of a double-stranded oligo RNA.

An object of the present invention is to find out that a RNAi function varies depending on positions of the hydrophilic materials and the hydrophobic materials bound to the double-stranded oligo RNA structure, and thus, is to provide a technology of delivering the SAMiRNA in which RNAi functions are maximized by optimization of the double-stranded oligo RNA structure forming the SAMiRNA.

The double-stranded oligo RNA structure according to the present invention has a form in which the hydrophilic materials and the hydrophobic materials helping delivery into a cell are bound to the RNA by a simple covalent bond or a linker-mediated covalent bond to be capable of being self-assembled as the nanoparticle (SAMiRNA) in an aqueous solution, which may be used as an RNA inhibitor with a high efficacy significantly usable for treatment of cancer and infectious diseases, and the like, and may also be used as a pharmaceutical composition containing the double-stranded oligo RNA structure for treatment of diseases. In particular, an RNA inhibiting activity with a high efficacy may be provided even at a low concentration of the SAMiRNA dosage and thus could be used as a therapeutic agent of cancer and infectious diseases, and the like.

In particular, the double-stranded oligo RNA structure according to the present invention may use the SAMiRNA which is a nanoparticular synthetic oligo RNA inhibitor and may maximize an efficacy in gene-specifically inhibiting RNA through a binding of the hydrophilic materials and the hydrophobic materials and 5' phosphorylation of an antisense strand in the SAMiRNA so as to have an optimized activity in vivo.

Figure 3:
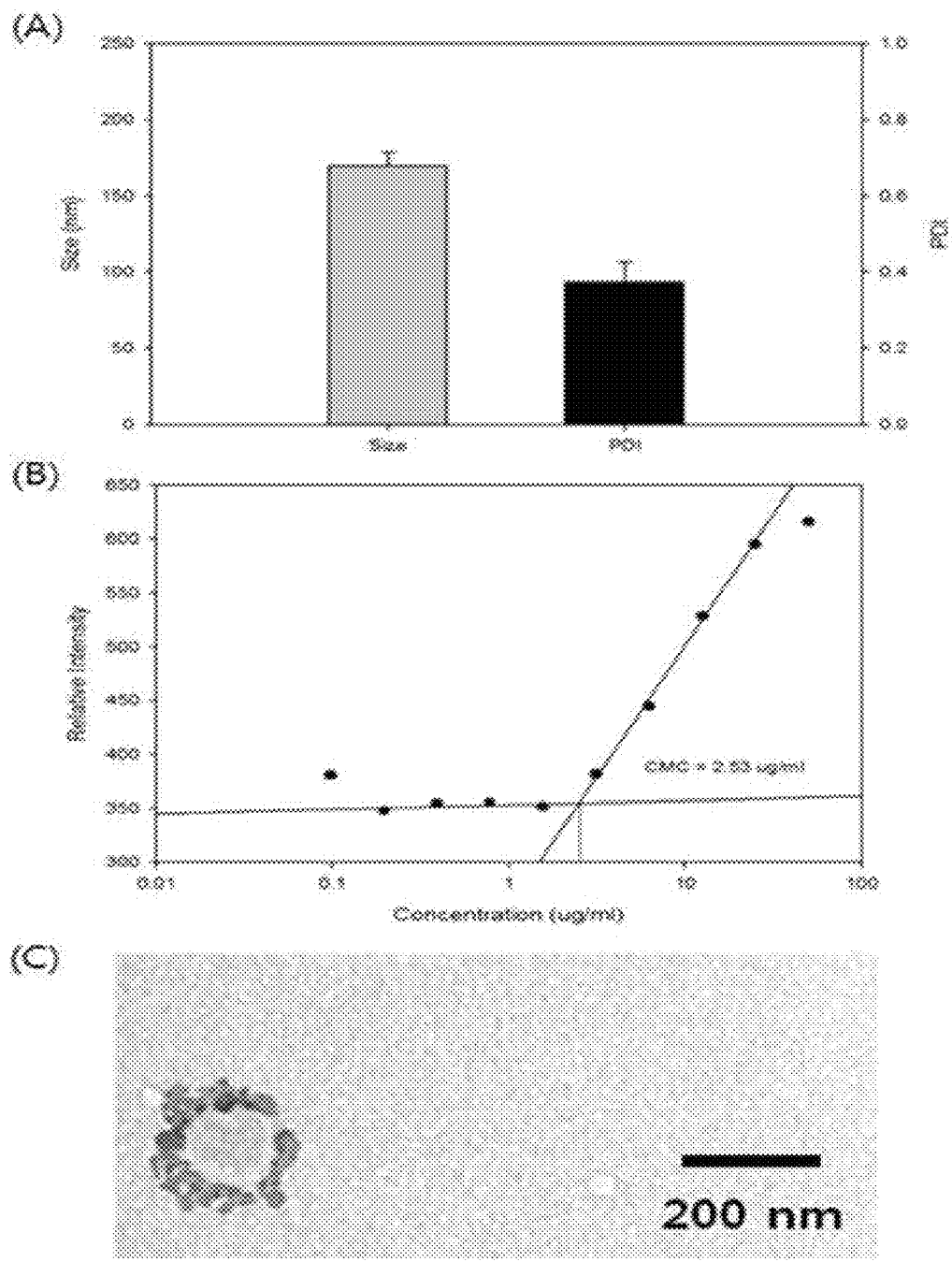
Figure 4:
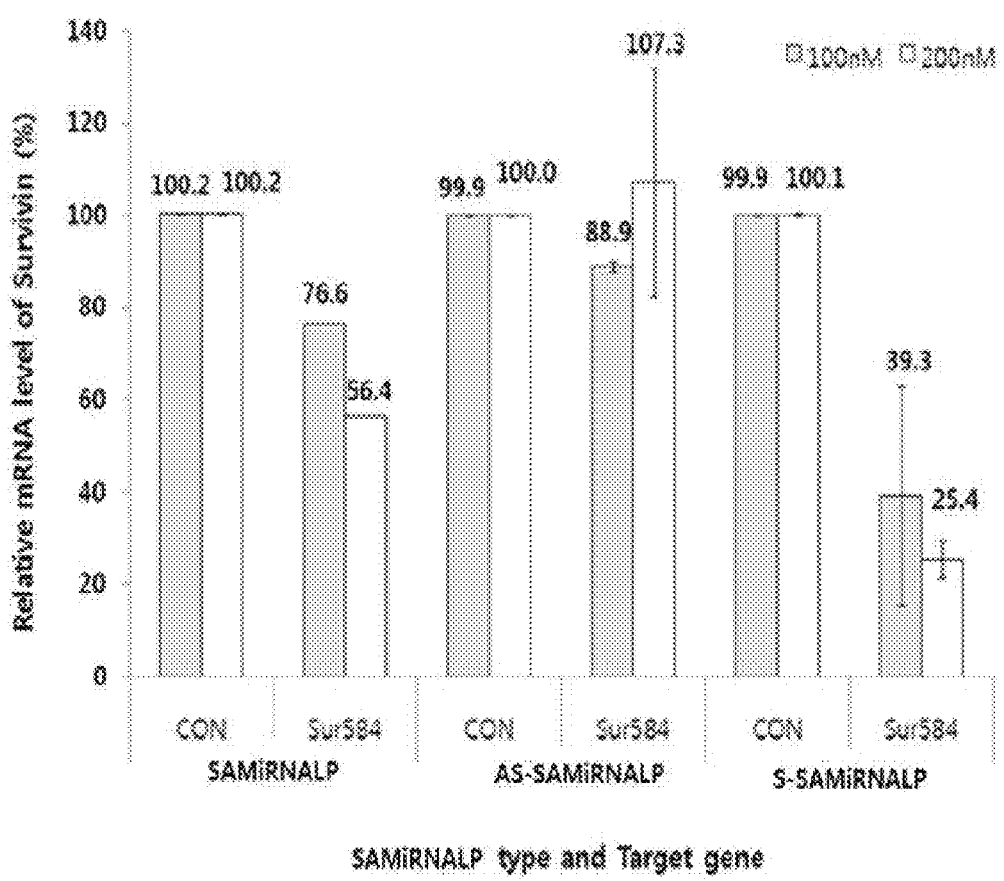
Figure 5:
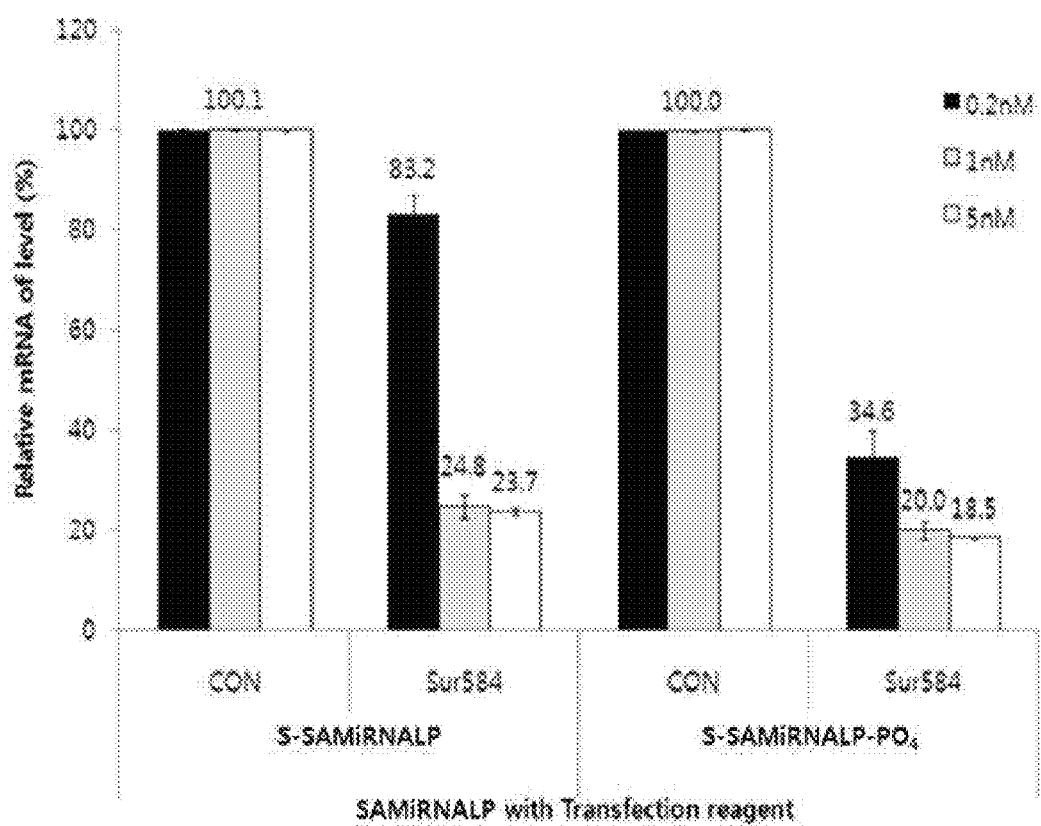

(A) MALDI-TOF MS analysis result of RNA single strand (blue, M.W. 6593.1) of a complementary sequence to SEQ ID NO: 1;

(B) MALDI-TOF MS analysis result of a form (Red, M.W. 6673.1) in which one phosphate group is bound to 5'end of the RNA single strand of a complementary sequence to SEQ ID NO: 1;

(C) MALDI-TOF MS comparison graph depending on the phosphate group bound to the RNA single strand of a complementary sequence to SEQ ID NO: 1, which is confirmed that as compared to a sequence in which the phosphate group is not bound (shown as blue), a case where one phosphate group is bound (shown as red) shows an increase as much as a molecular weight of the phosphate group (about MW 80);

FIG. 3 shows a physical property analysis result of the nanoparticle (SAMiRNA) of the double-stranded oligo RNA structure optimized according to the present invention;

(A) A graph of a size of the nanoparticle and polydispersity index (PDI);

(B) A graph of critical micelle concentration of the nanoparticle;

(C) An electron microscope photograph of the nanoparticle;

FIG. 4 is a graph obtained by treating the nanoparticle (SAMiRNA) consisting of a double-stranded oligo RNA structure in a HeLa cell line and confirming an effect of inhibiting an expression of a target gene by Quantitative real time PCR; and FIG. 5 is a graph obtained by treating the double-stranded oligo RNA structure together with a transfection material in a HeLa cell line and confirming an effect of inhibiting an expression of a target gene by Quantitative real time PCR.

BEST MODE

Hereinafter, the present invention will be described in detail.

The present invention provides a double-stranded oligo RNA structure to which a chemical material having a structure represented by the following formula 1 is bound:

$$\begin{array}{c} \text{A-X-S-Y-B} \\ \text{AS} \end{array} \quad \text{Formula 1}$$

wherein, one of A and B is a hydrophilic material, the other one is a hydrophobic material, X and Y are each a simple covalent bond or a linker-mediated covalent bond independently of each other, S is a sense strand of the double-stranded oligo RNA, and AS is an antisense strand of the double-stranded oligo RNA. S and AS configure a double-stranded structure by complementary binding, wherein the complementary binding is necessarily not a perfect complementary (perfect match) binding and may include a case where sequences are partially different (mismatch).

In addition, the present invention provides a double-stranded oligo RNA structure having a structure represented by the following formula 2:

$$\begin{array}{c} \text{A-X-S-Y-B} \\ \text{pAS} \end{array} \quad \text{Formula 2}$$

wherein, one of A and B is a hydrophilic material, the other one is a hydrophobic material, X and Y are each a simple covalent bond or a linker-mediated covalent bond independently of each other, S is a sense strand of the double-stranded oligo RNA, and pAS is an antisense strand in which a phosphate group is bound to 5' end portion of the double-stranded oligo RNA. Here, from one up to three of the phosphate group may be bound to 5' end portion.

It is preferred that the double-stranded oligo RNA strand consists of 19 to 31 nucleotides in the double-stranded oligo RNA structure of the present invention. As the double-stranded oligo RNA usable in the present invention, a double-stranded oligo RNA to any gene used for gene therapy or gene study or having a possibility therefore may also be adopted.

The double-stranded oligo RNA has various modifications for providing resistance of nuclease and decreasing a non-specific immune stimulation in order to improve stability in vivo, wherein the modification may be one or two or more combinations selected from modification in which —OH group at 2' carbon in a sugar structure in one or more nucleotides is substituted. with —CH(methyl), —OCH$_3$(methoxy), —NH$_2$, —F(fluorine), —O-2-methoxyethyl-O-propyl, —O-2-methylthioethyl, —O-3-aminopropyl, —O-3-dimethylaminopropyl, —O—N-methylacetamido or —O-dimethylamidooxyethyl; modification in which oxygen in a sugar structure in nucleotides is substituted with sulfur; and modification to phosphorothioate or boranophosphate, methyl phosphonate bindings from bindings among nucleotides, or may be modification to peptide nucleic acid (PNA), locked nucleic acid (LNA) or unlocked nucleic acid (UNA) (see Crooke et al., Ann. Rev. Med. Vol. 55: pp 61-65 2004, U.S. Pat. No. 5,660,985, U.S. Pat. No. 5,958,691, U.S. Pat. No. 6,531,584, U.S. Pat. No. 5,808,023, U.S. Pat. No. 6,326,358, U.S. Pat. No. 6,175,001 Braasch D. A. et al., Bioorg. Med. Chem. Lett. 14:1139-1143, 2003; Chiu Y. L. et al., RNA, 9:1034-1048, 2003; Amarzguioui M. et al., Nucleic Acid Res. 31:589-595, 2003, Nucleic Acids Research, 2010, Vol. 38, No. 17 5761-5775, Nucleic Acids Research, 2011, Vol. 39, No. 5 1823-1832).

The hydrophobic material serves to generate a hydrophobic interaction to form the nanoparticle (SAMiRNA) consisting of the double-stranded oligo RAN structures. Particularly, among the hydrophobic materials, carbon chain or cholesterol has an easy binding ability in synthesis of the double-stranded oligo RNA structure, which is significantly appropriate for preparation of the double-stranded oligo RNA structure of the present invention.

In addition, it is preferred that the hydrophobic material has a molecular weight of 250 to 1,000.

In particular, the hydrophobic material may include a steroid derivative, a glyceride derivative, glycerol ether, polypropylene glycol, unsaturated or saturated hydrocarbons containing 12 to 50 carbon atoms in a case of hydrocarbon chain, diacylphosphatidylcholine, fatty acid, phospholipid, lipopolyamine, and the like, as an example; but is not limited thereto. It is apparent to those skilled in the art that any hydrophobic materials are capable of being used as long as a material is to meet objects of the present invention.

In particular, the steroid derivative may be selected from a group consisting of cholesterol, cholestanol, cholic acid, cholesteryl formate, cholestanyl formate, and cholestanyl amine, and the glyceride derivative may be selected from mono-, di- and tri-glyceride, and the like, wherein a fatty acid of the glyceride is a $C_{12}$ to $C_{50}$ unsaturated or saturated fatty acid.

In addition, the hydrophilic material is preferably a cationic or non-ionic polymer material having a molecular weight of 200 to 10,000, more preferably, a non-ionic polymer material having a molecular weight of 1,000 to 2,000. For example, non-ionic hydrophilic polymer compounds such as polyethylene glycol, polyvinyl pyrrolidone, polyoxazoline, and the like, are preferably used as the hydrophilic polymer compound, but are not necessarily limited thereto.

The hydrophilic material may be modified by having functional groups required for binding with other materials such as a target specific ligand, and the like, as needed. Among the hydrophilic materials, in particular, polyethylene glycol (PEG) is significantly appropriate for preparing the double-stranded oligo RNA structure of the present invention since various molecular weights and functional groups may be introduced thereinto, affinity in vivo is excellent, an immune stimulation is not induced, bio-compatibility is excellent, stability of the double-stranded oligo RNA in vivo is increased, and a delivery efficiency is increased.

In addition, a linker mediating the covalent bond is covalently bound to the hydrophilic material (or a hydrophobic material) at an end of the double-stranded oligo RNA, but is not particularly limited as long as the bond which is degraded in a specific environment is provided as needed. Therefore, any compound for the binding to activate the oligo RNA and/or the hydrophilic material (or hydrophobic material) in preparation of the double-stranded oligo RNA structure may be used as the linker.

The covalent bond may be any one of a non-degradable bond or a degradable bond. Here, examples of the non-degradable bond may include an amide bond or phosphorylation bond, and examples of the degradable bond. may include disulfide bond, an acid degradable bond, an ester bond, an anhydride bond, a biodegradable bond or an enzymatically degradable bond, and the like, but the present invention is not necessarily limited thereto.

The present invention provides a double-stranded oligo RNA structure in which a hydrophobic material is bound to 5' end of a sense strand of the double-stranded oligo RNA and a hydrophilic material is bound to 3' end thereof as shown in the following formula 3, and a method of preparing the double-stranded oligo RNA structure may include:

$$\text{A-X-5' S 3'-Y-B} \atop \text{AS} \qquad \text{Formula 3}$$

wherein, A is a hydrophobic material, B is a hydrophilic material, X and Y are each a simple covalent bond or a linker-mediated covalent bond independently of each other, S is a sense strand of the double-stranded oligo RNA, and AS is an antisense strand of the double-stranded oligo RNA;

(1) synthesizing an RNA single strand based on a solid support containing a hydrophilic material bound thereto;

(2) preparing an RNA-polymer structure by covalently binding a hydrophobic material to 5' end of the RNA containing the hydrophilic material bound thereto;

(3) separating the RNA-polymer structure from the solid support; and (4) forming the double-stranded oligo RNA structure by annealing the RNA-polymer structure and an RNA single strand of a complementary sequence thereto.

More preferably, the method may include:

(1') binding a hydrophilic material based on a solid support, preferably, CPG;

(2)') synthesizing an RNA single strand based on the solid support (CPG) containing the hydrophilic material bound thereto;

(3') preparing an RNA-polymer structure by covalently binding a hydrophobic material to 5' end of the RNA single strand;

(4') separating the RNA-polymer structure from the solid support (CPG) when the synthesis is completed;

(5') forming the double-stranded oligo RNA structure by annealing the RNA-polymer structure and an RNA single strand of a complementary sequence thereto.

After the step (4) or (5') above, when the preparation is completed, the reactant may be purified by high performance liquid chromatography (HPLC) and a molecular weight thereof may be measured by MALDI-TOF mass spectrometry to confirm whether or not a desired double-stranded oligo RNA and a double-stranded oligo RNA structure are prepared.

In the preparation method thereof, the synthesizing of the RNA single strand of a complementary sequence to a sequence of the RNA single strand synthesized in the step (1) or (2'), which is an independent synthesis process, may be performed before the step (1) or the step (1') or may be performed during any one step of the steps (1) to (4) or (1') to (5').

In addition, the RNA single strand of a complementary sequence to the RNA single strand synthesized in the step (1) or (2') may contain a phosphate group bound to 5' end thereof as shown in the following formula 4:

$$\text{A-X-5' S 3'-Y-B} \atop \text{pAS} \qquad \text{Formula 4}$$

wherein, A is a hydrophobic material, B is a hydrophilic material, X and Y are each a simple covalent bond or a linker-mediated covalent bond independently of each other, S is a sense strand of the double-stranded oligo RNA, and pAS is an antisense strand in which a phosphate group is bound to 5' end portion of the double-stranded oligo RNA. Here, from one up to three of the phosphate group may be bound to 5' end portion.

The present invention provides a double-stranded oligo RNA structure in which a hydrophilic material is bound to 5' end of a sense strand of the double-stranded oligo RNA and a hydrophobic material is bound to 3' end thereof as shown in the following formula 5, and a method of preparing the double-stranded oligo RNA structure may include:

$$\text{B-X-5' S 3'-Y-A} \atop \text{AS} \qquad \text{Formula 5}$$

wherein, A is a hydrophobic material, B is a hydrophilic material, X and Y are each a simple covalent bond or a linker-mediated covalent bond independently of each, S is a sense strand of the double-stranded oligo RNA, and AS is an antisense strand of the double-stranded oligo RNA;

(1") synthesizing an RNA single strand based on a solid support containing a functional group bound thereto;

(2") covalently binding a hydrophilic material to the material obtained by the step (1");

(3") separating the material obtained by the step (2") from the solid support;

(4") forming the RNA-polymer structure by covalently binding a hydrophobic material through a functional group bound to 3' end of the material obtained by the step (3"); and (5") forming the double-stranded oligo RNA structure by annealing the RNA-polymer structure prepared by the step (4") and an RNA single strand of a complementary sequence thereto.

The functional group of the present invention is not limited as long as objects of the present invention may be achieved, preferably, may be selected from amine, thiol, carboxyl, aldehyde, biotin, and the like, In addition, the preparation method of the double-stranded oligo RNA structure may include: forming an RNA single strand based on a solid support containing the hydrophobic material bound thereto, covalently binding a hydrophilic material thereto to thereby prepare an RNA polymer structure and forming the double-stranded oligo RNA structure by annealing the RNA single strand and an RNA single strand of a complementary sequence thereto.

After the step (5") above, when the preparation is completed, the reactant may be purified by high performance liquid chromatography (HPLC) and a molecular weight thereof may be measured by MALDI-TOF mass spectrometry to confirm whether or not a desired double-stranded oligo RNA and a double-stranded oligo RNA structure are prepared.

In the preparation method, the synthesizing of the RNA single strand of a complementary sequence to a sequence of the RNA single strand synthesized in the step (1"), which is an independent synthesis process, may be performed before the step (1") or may be performed during any one step of the steps (1") to (5").

In addition, the RNA single strand of a complementary sequence to the RNA single strand synthesized in the step (1") may contain a phosphate group bound to 5' end thereof as shown in the following formula 6:

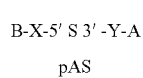

Formula 6 wherein, A is a hydrophobic material, B is a hydrophilic material, X and Y are each a simple covalent bond or a linker-mediated covalent bond independently of each other, S is a sense strand of the double-stranded oligo RNA, and pAS is an antisense strand in which a phosphate group is bound to 5' end portion of the double-stranded oligo RNA.

Meanwhile, in the double-stranded oligo RNA structure containing the ligand bound thereto of the present invention, a target specific ligand may be additionally provided with a specific position, in particular, an end, of the hydrophilic material bound to the double-stranded oligo RNA structure. The targeting moiety may be specifically bound to a receptor promoting internalization of a target cell, through receptor-mediated endocytosis (RME). The materials may be a target specific antibody, aptamer, peptide; or chemical materials including folate, N-acetyl galactosamine (NAG) and mannose, and the like, which are selected from a receptor specific ligand. Here, the targeting moiety may be any material as long as the material is specifically bound to the target receptor to perform the delivery, and thus, is not limited to the antibody, aptamer, peptide, and chemical materials.

The method of preparing the double-stranded oligo RNA structure containing a ligand bound thereto may include:

(1''') binding a hydrophilic material to a solid support (CPG) containing a functional group bound thereto;

(2''') synthesizing an RNA single strand based on the solid support (CPG) containing a functional group-hydrophilic material bound thereto;

(3''') preparing a functional group-RNA-polymer structure by covalently binding a hydrophobic material to 5' end of the RNA single strand;

(4''') separating the functional group-RNA-polymer structure from the solid support (CPG);

(5''') binding a ligand to an end of the hydrophilic material using the functional group to prepare an RNA polymer structure containing the ligand bound thereto; and (6''') preparing the double-stranded oligo RNA structure containing the ligand bound thereto by annealing the prepared RNA polymer structure containing the ligand bound thereto and an RNA single strand of a complementary sequence thereto.

The functional group of the present invention is not limited as long as objects of the present invention may be achieved, preferably, may be selected from amine, thiol, carboxyl, aldehyde, biotin, and the like.

After the step (6''') above, when the preparation is completed, the double-stranded oligo RNA structure containing the reactant and the ligand bound thereto and the RNA single strand of a complementary sequence thereto may be separated and purified by high performance liquid chromatography (HPLC) and molecular weights thereof may be measured by MALDI-TOF mass spectrometry to confirm whether or not a desired double-stranded oligo RNA structure containing the ligand bound thereto and RNA complementary thereto are prepared. In the preparation method, the synthesizing of the RNA single strand of a complementary sequence to a sequence of the RNA single strand synthesized in the step (2'''), which is an independent synthesis process, may be performed before the step (1''') or may be performed during any one step of the steps (1''') to (6''').

In addition, the present invention provides a nanoparticle (SAMiRNA) consisting of the double-stranded oligo RNA structure containing the ligand bound thereto. The double-stranded oligo RNA structure is amphipathic containing both of hydrophobic materials and hydrophilic materials, wherein the hydrophilic materials have affinity through an interaction such as hydrogen bond, and the like, with water molecules present in the body to be toward the outside and the hydrophobic materials are toward the inside by a hydrophobic interaction therebetween, thereby forming a thermodynamically stable nanoparticle (SAMiRNA). That is, the hydrophobic material is positioned in the center of the nanoparticle and the hydrophilic material is positioned in an outside direction of the double-stranded oligo RNA, thereby forming the nanoparticle protecting the double-stranded oligo RNA (see FIG. 1). The formed nanoparticle may improve the intracellular delivery of the double-stranded oligo RNA and the function thereof, and may be utilized for a purpose of treating diseases. More specific synthesis of the structure and characteristics, intracellular delivery efficiency and effects of the nanoparticle (SAMiRNA) consisting of the double-stranded oligo RNA structure will be described by the following Examples in more detail.

In addition, the present invention provides a treatment method using the double-stranded oligo RNA structure or SAMiRNA.

Specifically, the present invention provides a treatment method including: preparing nanoparticle (SAMiRNA) consisting of the double-stranded oligo RNA structure and administrating the nanoparticle (SAMiRNA) to the body of an animal.

In addition, the present invention provides a pharmaceutical composition containing a pharmaceutically effective amount of the double-stranded oligo RNA structure or the nanoparticle (SAMiRNA) consisting of the double-stranded oligo RNA structure.

The composition of the present invention may be prepared by additionally containing at least one kind of pharmaceutically acceptable carrier in addition to the above-described effective components for administration. The pharmaceutically acceptable carrier is required to be compatible with the effective components of the present invention. One component selected from saline, sterile water, Ringer's solution, buffered saline, dextrose solution, maltodextrin solution, glycerol, ethanol and other components or a combination of two or more components thereof may be used, and other conventional additives such as antioxidant, buffer, fungistat, and the like, may be added thereto as needed. In addition, the composition may be prepared as a formulation for injection, such as an aqueous solution, suspension, emulsion, and the like, by additionally adding diluent, dispersant, surfactant, binder and lubricant thereto. In particular, it is preferred that the composition is prepared as a lyophilized formulation. To prepare the lyophilized formulation, any method which is generally known in the corresponding art of the present invention may be used, wherein a stabilizer for lyophilization may be added thereto.

In addition, appropriate methods in the art or a method disclosed in Remington's pharmaceutical Science, Mack Publishing company, Easton Pa. may be preferably used for formulation depending on each disease or component.

The pharmaceutical composition of the present invention may be determined based on symptoms of the general patient and severity of the disease by a general expert in the art. In addition, the composition may be formulated with various types such as powder, tablet, capsule, solution, injection, ointment, syrup, and the like, and may be provided as a unit-dosage or a multi-dosage container, for example, a sealed ampoule, bottle, and the like.

The pharmaceutical composition of the present invention may be orally or parenterally administered. Examples of an administration route of the pharmaceutical composition according to the present invention may include oral, intravenous, intramuscular, intra-arterial, intramedullary, intradural, intracardiac, transdermal, subcutaneous, intraperitoneal, intestinal, sublingual topical administration, but the present invention is not limited thereto.

For the clinical administration as described above, the pharmaceutical composition of the present invention may be prepared as an appropriate formulation by known technology. The dosage of the composition may have various ranges thereof depending on weight, age, gender, health condition, diet, administration time, method, excretion rate the severity of disease, and the like, of patient, and may be easily determined by a general expert in the art.

The present invention provides a method of regulating gene expression in vivo or in vitro, using the double-stranded oligo RNA structure. In addition, the present invention provides a method of regulating gene expression in vivo or in vitro, using the nanoparticle containing the double-stranded oligo RNA structure.

Hereinafter, the present invention will be described in detail with reference to the following Examples. These examples are only for exemplifying the present invention, and it will be obvious to those skilled in the art that the scope of the present invention is not construed to be limited to these examples.

Example 1

Preparation of Double-Stranded Oligo RNA Structure

Hereinafter, in order to inhibit Survivin, a double-stranded oligo RNA to Survivin was used. The Survivin, which is protein commonly expressed in most neoplastic tumors or transformed cell lines tested until now, is expected as an important target in cancer treatment (Survivin: a new target for anti-cancer therapy. Cancer Treat Rev. 2009 November; 35(7): 553-62).

The double-stranded oligo RNA to Survivin of the present invention consists of a sense strand of SEQ ID NO: and an antisense strand of a complementary sequence thereto, and a double-stranded oligo RNA used as a control group consists of a sense strand of SEQ ID NO: 2 and an antisense strand of a complementary sequence thereto. Sequence of the double-stranded oligo RNA used in the present Examples is as follows:

(SEQ ID NO: 1) 5'-AAG GAG AUC AAC AUU UUC A-3'
(SEQ ID NO: 2) 5'-CUU ACG CUG AGU ACU UCG A-3'

In the double-stranded oligo RNA, the double-stranded oligo RNA single strand was synthesized by a method of using β-cyanoethylphosphoramidite to connect phosphodiester bonds configuring an RNA framework (Polymer support oligonucleotide synthesis XVIII: use of beta-cyanoethyl-N,N-dialkylamino-/N-morpholinophosphoramidite of deoxynucleosides for the synthesis of DNA fragments simplifying deprotection and isolation of the final product. Nucleic Acids Res. 1984 Jun. 11; 12(11): 4539-57).

A desired sequence of the RNA single strand is obtained by starting the synthesis process on the solid support (CPG) containing nucleoside bound thereto and repeating a cycle including deblocking, coupling, capping, and oxidation. The RNA 384 Synthesizer (BIONEER, Korea) was used for a series of the corresponding synthesis process of the double-stranded oligo RNA.

By comparison between the double-stranded oligo RNA configuring the double-stranded oligo RNA structure and the double-stranded oligo RNA depending on a binding side of a polymer material in view of an efficacy of inhibiting expression of a target gene, the double-stranded oligo RNA structures having the following structures were prepared for optimization of the double-stranded oligo RNA structure.

The double-stranded oligo RNA structures prepared in the present invention have structures shown in the following Table 1, respectively.

TABLE 1

| Name of Structure | Structure | Details |
|---|---|---|
| Double strand oligo RNA | S<br>AS | No hydrophilic and hydrophobic material bound to double-stranded oligo RNA |
| SAMiRNALP | PEG-5'S AS<br>5'-$C_{24}$ | double-stranded oligo RNA structure comprising hydrophilic and hydrophobic material bound to 5' end of sense and antisense strand of double-stranded oligo RNA |
| S-SAMiRNALP | $C_{24}$-5'S 3'-PEG AS | double-stranded oligo RNA structure comprising hydrophilic and hydrophobic material bound to sense strand of double-stranded oligo RNA |
| AS-SAMiRNALP | S PEG-3' AS<br>5'-$C_{24}$ | double-stranded oligo RNA structure comprising hydrophilic and hydrophobic material bound to antisense strand of double-stranded oligo RNA |
| S-SAMiRNALP-$PO_4$ | $C_{24}$-5'S 3'-PEG<br>3' AS 5'-$PO_4$ | double-stranded oligo RNA structure comprising hydrophilic and hydrophobic material bound to sense strand and phosphate group bound to antisense strand of double-stranded oligo RNA |

In Table 1, S is a sense strand of the double-stranded oligo RNA; AS is an antisense strand of the double-stranded oligo RNA; $PO_4$ is a phosphate group; PEG is a hydrophilic material: polyethylene glycol; $C_{24}$ is a hydrophobic material: tetradocosane containing a bisulfide bond; and 5' and 3' mean directionality of an end of the double-stranded oligo RNA.

The synthesis of the sense strand of the double-stranded oligo RNA structure was performed using β-cyanoethylphosphoramidite to connect phosphodiester bonds configuring an RNA framework as described above and polyethylene glycol (PEG) was additionally bound to 5' end portion thereof, thereby preparing a sense strand of SAMiRNALP of the double-stranded oligo RNA structure.

In a case of an antisense strand performing an annealing with the sense strand of the double-stranded oligo RNA structure, the synthesis of the antisense strand was performed using β-cyanoethylphosphoramidite to connect phosphodiester bonds configuring an RNA framework as described above, then tetradocosane ($C_{24}$) containing a bisulfide bond which is the hydrophobic material, was additionally bound to 5' end portion thereof, thereby preparing an antisense strand of SAMiRNALP.

A desired sense strand of S-SAMiRNALP was prepared by performing the reaction having 3' polyethylene glycol (PEG)-CPG prepared by Example 1 of the related art document (Korean Patent Laid-Open Publication No. 2009-0042297) as a support, to synthesize a double-stranded oligo RNA-hydrophilic material structure having a sense strand containing PEG bound to 3' end portion thereof, and binding tetradocosane($C_{24}$) containing a bisulfide bond to 5' end. In a case of an antisense strand annealing with the sense strand of the S-SAMiRNALP, the antisense strand of a complementary sequence to the sense strand was prepared by a method of using β-cyanoethylphosphoramidite to connect phosphodiester bonds configuring an RNA framework as described above.

A sense strand of AS-SAMiRNALP was prepared by a method of using β-cyanoethylphosphoramidite to connect phosphodiester bonds configuring an RNA framework as described above.

A desired antisense strand performing an annealing with the sense strand of the AS-SAMiRNALP was prepared by performing the reaction having 3' PEG-CPG prepared by Example 1 of the related art document (Korean Patent Laid-Open Publication No. 2009-0042297) as a support, to synthesize a double-stranded oligo RNA-hydrophilic polymer structure having an antisense strand containing PEG bound to 3' end portion thereof, and binding tetradocosane($C_{24}$) containing a bisulfide bond to 5' end.

In order to maximize an effect of the double-stranded oligo RNA, S-SAMiRNALP-$PO_4$ has a sense strand containing a structure of hydrophilic materials and hydrophobic materials bound thereto and an antisense strand containing a phosphate group bound to 5' end portion thereof.

Figure 2:
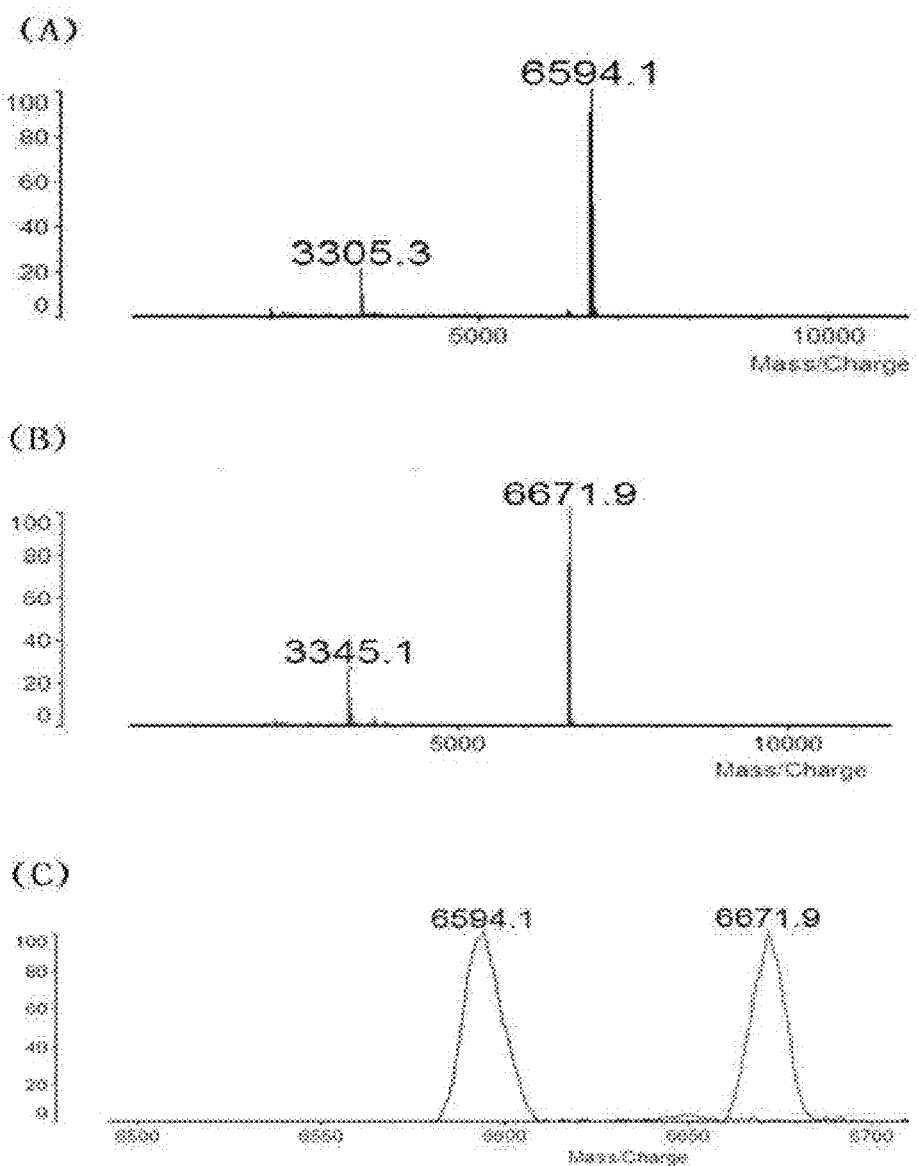
FIG. 2 is a view showing preparation result of an antisense strand of S-SAMiRNALP-PO$_4$.

A sense strand of S-SAMiRNALP-$PO_4$ was prepared by the same method as the sense strand of S-SAMiRNALP, and an antisense strand performing an annealing of the S-SAMiRNALP-$PO_4$ containing a phosphate group bound to 5' end was prepared by performing the reaction using β-cyanoethylphosphoramidite to connect phosphodiester bonds configuring an RNA framework as described above and then, using chemical phosphorylation reagent (CPR) which is [3-(4,4'Dimethoxytrityloxy)-2,2-dicarboxyethyl]propyl-(2-cyanoethyl)-(N, N-diisopropyl)-phosphoramidite to bind a phosphate group to 5' end (see FIG. 2). Otherwise, the antisense strand of S-SAMiRNALP-$PO_4$ containing a phosphate group bound thereto was prepared by using a method comprising collecting the RNA single strand from CPG and treating a phosphorylation enzyme (kinase) to bind the phosphate group to 5' end.

When the synthesis was completed, the synthesized RNA single strand and the RNA-polymer structure were separated from CPG with 28%(v/v) ammonia in a water bath at 60° C. and protecting moiety was removed by deprotection reaction. The RNA single strand and the RNA-polymer structure from which the protecting moiety was removed were treated with N-methylpyrrolidone, triethylamine and triethylaminetrihydrofluoride at a volume ratio of 10:3:4, in an oven at 70° C., to remove 2' TBDMS(tert-butyldimethylsilyl).

In addition, in order to bind a ligand to the end portion of the hydrophilic polymer of the double-stranded oligo RNA structure, functional groups capable of binding the ligand was bound to 3' CPG, the hydrophilic polymer was bound thereto, and the reaction was performed, thereby preparing the sense strand of the SAMiRNALP to which the ligand is capable of being bound. In more detail, 3' amine-PEG-RNA was synthesized using a PEG phosphoramidite reagent in amine-CPG containing functional groups such as amine groups, and the like, bound thereto and a hydrophobic material such as $C_{24}$ was bound to the 3' amine-PEG-RNA oligo to synthesize 3' amine-PEG-RNA-$C_{24}$, followed by treatment with 28%(v/v) ammonia in a water bath at 60° C. to separate the synthesized RNA single strand and the RNA-polymer structure from CPG and the protecting moiety was removed by deprotection reaction. The RNA single strand and the RNA-polymer structure from which the protecting moiety was removed were treated with N-methylpyrrolidone, triethylamine and triethylaminetrihydrofluoride at a volume ratio of 10:3:4, in an oven at 70° C., to remove 2' TBDMS(tert-butyldimethylsilyl). The collected 3' amine-PEG-RNA-$C_{24}$ therefrom was subjected to an ester reaction with a bindable ligand material consisting of N-Hydroxysuccinimide ligand to synthesize a 3' ligand-bound PEG-RNA-$C_{24}$ oligo. The RNA single strand, the RNA-polymer structure, and the RNA-polymer structure containing the ligand bound thereto were separated from the reactants by HPLC, and molecular weights thereof were measured by MALDI-TOF-MS (SHIMADZU, Japan) to confirm whether or not sequence and the RNA-polymer structure correspond to those to be synthesized.

Then, in order to prepare each double-stranded oligo RNA structure, the sense strand and the antisense strand in an equivalent amount were mixed to each other and put into IX annealing buffer (30 mM HEPES, 100 mM potassium acetate, 2 mM magnesium. acetate, pH 7.0 to 7.5), followed by reaction in a constant temperature water bath at 90° C. for 3 minutes and then reaction at 37° C., thereby preparing the desired SAMiRNALP and the desired S-SAMiRNALP-$PO_4$ containing a phosphate group bound thereto, respectively. Annealing of the prepared SAMiRNALP was confirmed by electrophoresis.

Example 2

Analysis of Physical Property of Nanoparticle (SAMiRNA) Consisting of SAMiRNALP

Figure 1:
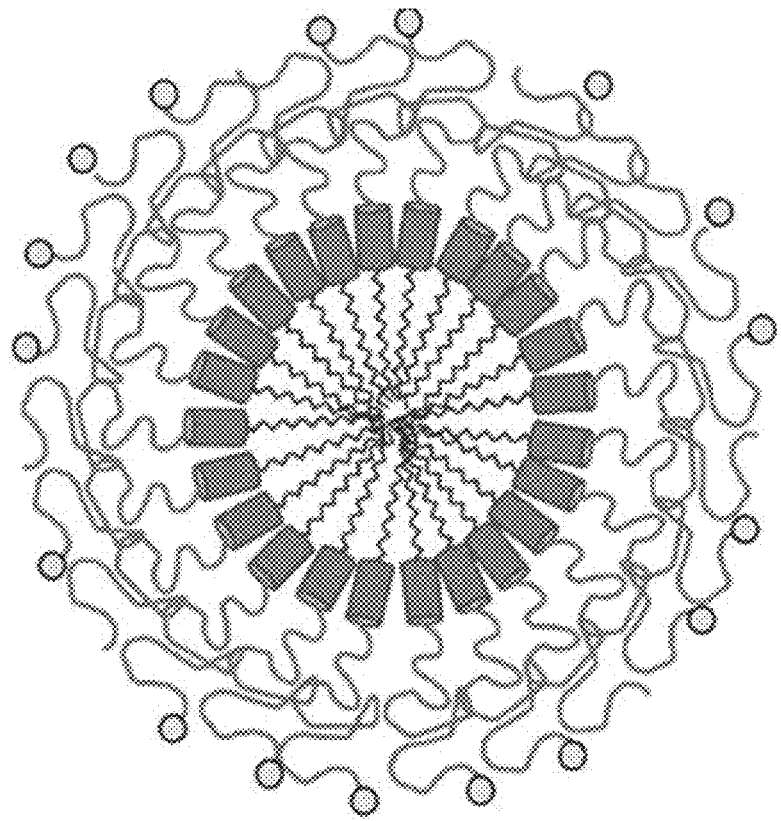
FIG. 1 is a schematic view of nanoparticles (SAMiRNA) containing a double-stranded oligo RNA structure.

S-SAMiRNALP and S-SAMiRNALP-$PO_4$ forms a nanoparticle, that is, micelle, by a hydrophobic interaction between the hydrophobic materials bound to the end of the double-stranded oligo RNA (see FIG. 1).

Formation of the nanoparticle (SAMiRNA) consisting of the corresponding SAMiRNALP was confirmed by analysis of nanoparticle size, critical micelle concentration (CMC) and Transmission Electron Microscope (TEM) of the S-SAMiRNALP prepared by Example 1 above.

Example 2-1

Measurement of Particle Size and Polydispersity Index (PDI) of Nanoparticle Consisting of SAMiRNALP A size of the nanoparticle was measured by zeta-potential measurement. In detail, the SAMiRNALP was dissolved into 1.5 ml of Dulbecco's phosphate buffered saline (DPBS) so as to have a concentration of 50 µg/ml and then treated by a ultrasonic homogenizer (Wiseclean, DAIHAN, Korea) so that a size of nanoparticle is homogenized (700 W; amplitude: 20%). A size of the homogenized nanoparticle was measured by zeta-potential measurement (Nano-ZS, MALVERN, England) under conditions in which a refractive index to the material is 1.459, an absorption index is 0.001, a temperature of a solvent: PBS is 25° C. and the corresponding viscosity and refractive index are 1.0200 and 1.335, respectively. Once measurement was conducted by a size measurement including 20 times repeats and then repeated three times.

It was confirmed that the nanoparticle consisting of S-SAMiRNALP had a size of about 150 nm and PDI of about 0.4 (see FIG. 3(A)). As the PDI is low, the corresponding particles become uniformly distributed, and thus, it could be appreciated that the nanoparticle consisting of S-SAMiR-NALP has a relatively uniform size. It was confirmed that the size of the nanoparticle consisting of the structure has an appropriate size to be intaken in the cell through endocytosis (Nanotoxicology: nanoparticles reconstruct lipids. Nat. Nanotechnol. 2009 February; 4(2):84-5).

Example 2-2

Measurement of Critical Micelle Concentration (CMC) of Nanoparticle Consisting of SAMiRNALP An amphiphile containing both of hydrophobic materials and hydrophilic materials in a single molecule may be a surfactant, wherein when the surfactant is dissolved into an aqueous solution, the hydrophobic groups thereof move toward the center portion to prevent water contact and the hydrophilic groups thereof moves toward the outside to form micelle. Here, a concentration at which the micelle is initially formed is referred to as a critical micelle concentration (CMC). A method of measuring CMC using fluorescent pigment is based on property of the fluorescent pigment in which the slope of the graph curve of the fluorescence intensity is rapidly changed before/after the micelle is formed.

In order to measure CMC of the nanoparticle consisting of S-SAMiRNALP, 0.04 mM DPH (1,6-Diphenyl-1,3,5-hexatriene, SIGMA, USA) was prepared as the fluorescent pigment. 1 nmole/µl of S-SAMiRNALP was diluted from a concentration of 0.0977 µg/ml to the maximum of 50 µg/ml with DPBS for each step to prepare S-SAMiRNALP samples having the total volume of 180 µl. 20 µl of 0.04 mM DPH and methanol which is a solvent of DPH for a control group were added to the prepared samples, respectively and mixed well, and treated by a ultrasonic homogenizer (Wiseclean, DAIHAN, Korea) according to the same method as Example 2-1 so that a size of the nanoparticle is homogenized (700 W; amplitude: 20%). The homogenized samples were reacted at room temperature without light for about 24 hours, and fluorescent values (excitation: 355 nm, emission: 428 nm, top read) were measured. In order to confirm relative fluorescent values among the measured fluorescent values, the fluorescent value of the sample containing DPH and the fluorescent value of the sample containing the only methanol (Y axis) were measured and shown as a graph with respect to log value of the treated concentration of S-SAMiRNALP (X axis) (see FIG. 3(B)).

The fluorescent value measured for each concentration was rapidly increased while moving from a low concentration section to a high concentration section, wherein the concentration at the rapidly increased point is CMC concentration. Therefore, when drawing trend lines by dividing the low concentration section in which the fluorescent amount is not increased and the high concentration section in which the fluorescent amount is increased into several sections, an X value in an intersection of the two trend lines is CMC concentration. It was observed that the measured CMC of the nanoparticle consisting of S-SAMiRNALP is 2.53 µg/ml, which is significantly low, and thus, it was confirmed that the micelle may be formed by the nanoparticle consisting of S-SAMiRNALP even at a significantly low concentration.

Example 2-3

Observation of Nanoparticle Consisting of SAMiRNALP by TEM

The nanoparticle consisting of S-SAMiRNALP was observed by TEM in order to confirm the shape thereof.

In detail, the SAMiRNALP was dissolved into DPBS so as to have the final concentration of 100 µg/ml and treated by a ultrasonic hoginezer (Wiseclean, DAIHAN, Korea) so that a size of nanoparticle is homogenized (700 W; amplitude: 20%). The nanoparticle consisting of S-SAMiRNALP was observed with a material having a high electron density through a negative staining method (see FIG. 3(C)).

It was confirmed that the nanoparticle observed by TEM is well formed with a size similar to that of the nanoparticle measured in Example 2-1.

Example 3

Inhibition of Expression of Target Gene in Tumor Cell Line Using Nanoparticle Consisting of SAMiRNALP Expression of Survivin gene of a transfected tumor cell line was analyzed using each nanoparticle consisting of SAMiR-NALP, S-SAMiRNALP, or AS-SAMiRNALP prepared by Example 1 above.

Example 3-1

Culture of Tumor Cell Line

10% (v/v) fetal bovine serum, 100 units/ml of penicillin and 100 µg/ml of streptomycin were added to an EMEM. culture medium (ATCC-formulated eagle's minimum essential medium) containing HeLa acquired from American type Culture Collection (ATCC) and cultured at 37° C. and 5%(v/v) $CO_2$.

Example 3-2

Transformation of Tumor Cell Line Using Nanoparticle Consisting of SAMiRNALP

The tumor cell line ($1.3 \times 10^5$) cultured in Example 3-1 above were cultured in a 6-well plate in the EMEM culture medium for 18 hours under the same condition as Example 3-1 above, the medium was removed, and the equivalent amount of Opti-MEM medium per each well was deposited.

100 µl of the Opti-MEM medium and each 50 µg/ml of the SAMiRNALP, S-SAMiRNALP and AS-SAMiRNALP were added to DPBS, and then treated by a ultrasonic homoginezer (Wiseclean, DAIHAN, Korea) according to the same method as Example 2-1 to thereby homogenize (700 W; amplitude: 20) each nanoparticle consisting of SAMiRNALP, S-SAMiRNALP and AS-SAMiRNALP, thereby preparing solutions. Then, each well of the tumor cell line in which the Opti-MEM is deposited was treated with a transfection solution at a concentration of 100 nM and 200 nM, and cultured at 37° C. and 5%(v/v) $CO_2$ for the total of 48 hours.

Example 3-3

Relative Quantitative Analysis of mRNA of Survivin Gene

The total RNA was extracted from the transfected cell line in Example 3-2 above, cDNA was synthesized, and an expression amount of mRNA of Survivin was relatively quantitative analyzed by real-time PCR according to a method disclosed in Korean Patent Laid-Open Publication No. 2009-0042297 (see FIG. 4).

The nanoparticle consisting of AS-SAMiRNALP, which is a case in which the structure was bound to the only antisense strand bound to the target mRNA in the double-stranded oligo RNA mechanism, shows a low inhibiting efficacy as compared to the existing nanoparticle consisting of SAMiRNALP. The nanoparticle consisting of S-SAMiRNALP, which is a case in which the structure was bound to the only sense strand being contrary to the above case of nanoparticle consisting of AS-SAMiRNALP, shows a high inhibiting efficacy even at a low concentration as compared to the existing nanoparticle consisting of SAMiRNALP (see FIG. 4).

Sur584 means SAMiRNALP having double-stranded oligo RNA sequence (SEQ ID NO: 1) specific to the target gene Survivin according to each structures of SAMiRNALP, and CON means SAMiRNALP including control group sequence (SEQ ID NO: 2) not affecting expression of the target gene. A degree of inhibiting expression of mRNA of the target gene was calculated with the expression amount of the target gene of a sample treated with Sur584 with respect to the expression amount of the target gene of a sample treated with CON by Comparative Quantitation.

The nanoparticle consisting of S-SAMiRNALP which is the optimized structure was well delivered into the cell without a transfection material and thus, an effect of inhibiting expression of mRNA of the target gene was observed, which was confirmed to have an increase effect of the double-stranded oligo RNA by about three times or more (nanoparticle groups consisting of SAMiRNALP—23.4% inhibition vs. nanoparticle groups consisting of S-SAMiRNALP—77% inhibition) when being treated with 100 nM, as compared to the existing nanoparticle consisting of SAMiRNAL. In addition, it was observed that the Experimental group of the nanoparticle consisting of AS-SAMiRNALP in which all structures are bound to the antisense strand which is a negative control group has a low effect of inhibiting expression of mRNA of the target gene even at a high concentration.

Example 4

Inhibition of Expression of Target Gene in Tumor Cell Line Using SAMiRNALP

Each of S-SAMiRNALP of SEQ ID NO: 1 and S-SAMiRNALP-PO$_4$ of SEQ ID NO: 2 prepared by Example 1 above were transfected into Hela by a transfection material and expression of Survivin of the transfected tumor cell line was analyzed.

Example 4-1

Transfection of Tumor Cell Line Using SAMiRNALP

The tumor cell lines (1.3×10$^5$) cultured in Example 3-1 above were cultured in a 6-well plate in the EMEM culture medium for 18 hours under the same condition as Example 3-1 above, the medium was removed, and 8000 of Opti-MEM medium per each well was deposited.

Meanwhile, 2 μl of Lipofectamine™ RNAiMax (Invitrogen, USA) and 198 μl of Opti-MEM medium were mixed and reacted at room temperature for 5 minutes, and treated with each of the S-SAMiRNALP and S-SAMiRNALP-PO$_4$ (25 pmole/μl) prepared by Example 1 above so as to have the final concentration of 0.2, 1 and 5 nM, respectively, followed by reaction at room temperature for 20 minutes, thereby preparing solution.

Then, 200 μl of each transfection solution was deposited into each well of the tumor cell line containing Opti-MEM deposited therein and cultured for 6 hours, and Opti-MEM medium was removed. Here, 2.5 ml of EMEM culture medium was deposited thereto and cultured at 37° C. and 5%(v/v) $CO_2$ for 24 hours.

Example 4-2

Relative Quantitative Analysis of mRNA of Survivin Gene

The total RNA was extracted from the transfected cell line in Example 4-1 above, cDNA was synthesized, and an expression amount of mRNA of Survivin gene was analyzed based on relative quantification by real-time PCR according to a method disclosed in Korean Patent Laid-Open Publication No. 2009-0042297.

In order to analyze an effect of inhibiting expression of the target gene by S-SAMiRNALP and S-SAMiRNALP-PO$_4$, the transformation was conducted with the transfection material, and the degree of expression of mRNA of Survivin gene was measured, and thus, it could be confirmed that the cases treated with S-SAMiRNALP and S-SAMiRNALP-PO$_4$ show an effect of inhibiting expression of the target gene similar to that of the naked double-stranded oligo RNA in which nothing is bound to the end of the double-stranded oligo RNA. S-SAMiRNALP-PO$_4$ showed relatively high efficacy of inhibiting expression as compared to S-SAMiRNALP, and in particular, high effect of inhibiting expression of the target gene was shown at a low concentration of 0.2 nM (see FIG. 5). It was observed that the RNA structure containing S-SAMiRNALP polymer bound thereto does not inhibit mechanism of RNAi, and in particular, in S-SAMiRNALP-PO$_4$, an effect of double-stranded oligo RNA is increased by the additionally bound phosphate group.

INDUSTRIAL APPLICABILITY

The double-stranded oligo RNA structure or the pharmaceutical composition containing the same according to the present invention may be significantly used for treatment of various diseases, and particularly, may exhibit the RNA inhibiting activity with high efficacy even at a low concentration of the SAMiRNA dosage and could be used as a therapeutic agent of cancer and infectious diseases, and the like.

The invention claimed is:

1. A double-stranded oligo RNA structure to which a chemical material having a structure represented by the following formula 1 is bound:

Formula 1 wherein one of A and B is a hydrophilic material, the other one is a hydrophobic material, X and Y are each a simple covalent bond or a linker-mediated covalent bond independently of each other, S is a sense strand of the double-stranded oligo RNA, and AS is an antisense strand of the double-stranded oligo RNA.

2. The double-stranded oligo RNA structure according to claim 1, wherein the hydrophobic material is bound to 5' end of a sense strand of the double-stranded oligo RNA and the hydrophilic material is bound to 3' end thereof as shown in the following formula 3:

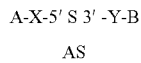

Formula 3 wherein A is a hydrophobic material, B is a hydrophilic material, X and Y are each a simple covalent bond or a linker-mediated covalent bond independently of each other, S is a sense strand of the double-stranded oligo RNA, and AS is an antisense strand of the double-stranded oligo RNA.

3. The double-stranded oligo RNA structure according to claim 1, wherein the sense and antisense strand of the double-stranded oligo RNA strand consists of 19 to 31 nucleotides.

4. The double-stranded oligo RNA structure according to claim 3, wherein nucleotide comprises one or two or more combinations of modifications selected from modification in which —OH group at 2' carbon in a sugar structure in one or more nucleotides is substituted with —CH$_3$(methyl), —OCH$_3$(methoxy), —NH$_2$, —F(fluorine), —O-2-methoxyethyl-O-propyl, —O-2-methylthioethyl, —O-3-aminopropyl, —O-3-dimethylaminopropyl, —O—N-methylacetamido or —O-dimethylamidooxyethyl; modification in which oxygen in a sugar structure in nucleotides is substituted with sulfur; and modification to phosphorothioate or boranophosphophate, methyl phosphonate bindings from bindings among nucleotides, and modification to peptide nucleic acid (PNA), locked nucleic acid (LNA) or unlocked nucleic acid (UNA).

5. The double-stranded oligo RNA structure according to claim 1, wherein phosphate group(s) is bound to 5' end of the antisense strand.

6. The double-stranded oligo RNA structure according to claim 5, wherein one to three phosphate group(s) is bound to 5' end of the antisense strand.

7. The double-stranded oligo RNA structure according to claim 1, wherein the hydrophobic material has a molecular weight of 250 to 1,000.

8. The double-stranded oligo RNA structure according to claim 7, wherein the hydrophobic material is selected from a group consisting of steroid derivative, a glyceride derivative, glycerol ether, polypropylene glycol, C12 to C50 unsaturated or saturated hydrocarbons, diacylphosphatidylcholine, fatty acid, phospholipid, lipopolyamine.

9. The double-stranded oligo RNA structure according to claim 8, wherein the steroid derivative is selected from a group consisting of cholesterol, cholestanol, cholic acid, cholesteryl formate, cholestanyl formate, and cholestanyl amine.

10. The double-stranded oligo RNA structure according to claim 8, wherein the glyceride derivative is selected from a group mono-, di- and tri-glyceride.

11. The double-stranded oligo RNA structure according to claim 1, wherein the hydrophilic material has a molecular weight of 200 to 10,000.

12. The double-stranded oligo RNA structure according to claim 11, wherein the hydrophilic material selected from a group consisting of polyethylene glycol, polyvinyl pyrrolidone, polyoxazoline.

13. The double-stranded oligo RNA structure according to claim 1, wherein the covalent bond is non-degradable bond or a degradable bond.

14. The double-stranded oligo RNA structure according to claim 13, wherein non-degradable bond is an amide bond or a phosphorylation bond.

15. The double-stranded oligo RNA structure according to claim 13, wherein the degradable bond is a disulfide bond, an acid degradable bond, an ester bond, an anhydride bond, a biodegradable bond or an enzymatically degradable bond.

16. The double-stranded oligo RNA structure according to claim 1, wherein the double-stranded oligo RNA specifically binds to a sequence of survivin mRNA.

17. The double-stranded oligo RNA structure according to claim 16, wherein sense strand of the double-stranded oligo RNA has the sequence of 5'-AAG GAG AUC AAC AUU UUC A-3' (SEQ ID NO:1).

18. A double-stranded oligo RNA structure containing a ligand bound thereto comprising a ligand bound to a hydrophilic material of the double-stranded oligo RNA structure according to claim 1.

19. The double-stranded oligo RNA structure containing a ligand bound thereto according to claim 18, wherein the ligand comprises a targeting moiety specifically bound to a receptor promoting internalization of a target cell, through receptor-mediated endocytosis (RME).

20. The double-stranded oligo RNA structure containing a ligand bound thereto according to claim 19, wherein the ligand is selected from a group consisting of target specific antibody, aptamer, peptide, and receptor specific chemical material.

21. The double-stranded oligo RNA structure containing a ligand bound thereto according to claim 20, wherein the receptor specific chemical material is selected from a group consisting of folate, N-acetyl galactosamine (NAG) and mannose.

22. A method of preparing a double-stranded oligo RNA structure comprising:
   (1) synthesizing an RNA single strand based on a solid support containing a hydrophilic material bound thereto;
   (2) preparing an RNA-polymer structure by covalently binding a hydrophobic material to 5' end of the RNA containing the hydrophilic material bound thereto;
   (3) separating the RNA-polymer structure from the solid support; and
   (4) forming the double-stranded oligo RNA structure by annealing the RNA-polymer structure and an RNA single strand of a complementary sequence thereto.

23. The method of preparing according to claim 22, wherein a complementary sequence of the RNA single strand in the step (1) comprises phosphate group(s) bound to 5' end of the RNA single strand.

24. A method of preparing a double-stranded oligo RNA structure comprising:
   (1) synthesizing an RNA single strand based on a solid support containing a functional group bound thereto;
   (2) covalently binding a hydrophilic material to the material obtained by the step (1);
   (3) separating the material obtained by the step (2) from the solid support;
   (4) forming the RNA-polymer structure by covalently binding a hydrophobic material through a functional group bound to 3' end of the material obtained by the step (3); and
   (5) forming the double-stranded oligo RNA structure by annealing the RNA-polymer structure prepared by the step (4) and an RNA single strand of a complementary sequence thereto.

25. The method of preparing according to claim 24, wherein a complementary sequence of the RNA single strand in the step (1) comprises phosphate group(s) bound to 5' end of the RNA single strand.

26. A nanoparticle comprising a double-stranded oligo RNA structure according to claim 1.

27. A nanoparticle comprising a double-stranded oligo RNA structure containing a ligand bound thereto according to claim 18.

28. A pharmaceutical composition comprising a double-stranded oligo RNA structure according to claim 1.

29. A pharmaceutical composition comprising a nanoparticle comprising a double-stranded oligo RNA structure containing a ligand bound thereto according to claim 18.

30. A pharmaceutical composition comprising a nanoparticle according to claim 26.

31. A pharmaceutical composition comprising a nanoparticle according to claim 27.

32. A method of controlling the expression of gene in vivo or in vitro by using a double-stranded oligo RNA structure according to claim 1.

33. A method of controlling the expression of gene in vivo or in vitro by using a nanoparticle according to claim 26.

* * * * *

UNITED STATES PATENT AND TRADEMARK OFFICE
CERTIFICATE OF CORRECTION

PATENT NO. : 9,326,941 B2  
APPLICATION NO. : 14/370035  
DATED : May 3, 2016  
INVENTOR(S) : Jeiwook Chae et al.

Page 1 of 1

It is certified that error appears in the above-identified patent and that said Letters Patent is hereby corrected as shown below:

In the Specification

Column 6, line 7: "CH (methyl)" should be -- $CH_3$ (methyl) --.

Signed and Sealed this  
Second Day of August, 2016

Michelle K. Lee  
*Director of the United States Patent and Trademark Office*

SEQUENCE LISTING

<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: double-stranded oligo RNA

<400> SEQUENCE: 1
aaggagauca acauuuuca                                                19

<210> SEQ ID NO 2
<211> LENGTH: 19
<212> TYPE: RNA
<213> ORGANISM: Artificial Sequence
<220> FEATURE:
<223> OTHER INFORMATION: double-stranded oligo RNA

<400> SEQUENCE: 2
cuuacgcuga guacuucga                                                19